United States Patent [19]

Brazdil, Jr. et al.

[11] Patent Number: 5,576,469

[45] Date of Patent: Nov. 19, 1996

[54] PARAFFIN AMMOXIDATION USING VANADIUM ANTIMONY OXIDE BASED CATALYSTS WITH HALIDE PROMOTERS

[75] Inventors: James F. Brazdil, Jr., Highland Heights; Fernando A. P. Cavalcanti, South Euclid, both of Ohio

[73] Assignee: The Standard Oil Co., Cleveland, Ohio

[21] Appl. No.: 461,997

[22] Filed: Jun. 5, 1995

[51] Int. Cl.$^6$ ..................................................... B01J 23/18
[52] U.S. Cl. ........................ 558/319; 558/320; 558/321; 558/322; 558/323; 558/324; 558/325
[58] Field of Search ..................................... 558/319, 320, 558/321, 322, 323, 324, 325

[56] References Cited

U.S. PATENT DOCUMENTS

| | | | |
|---|---|---|---|
| 3,746,737 | 7/1973 | Tullman et al. | 260/465.3 |
| 3,833,638 | 9/1974 | Knox et al. | 260/465.3 |
| 3,860,534 | 1/1975 | Harris et al. | 252/461 |
| 4,000,178 | 12/1976 | Kahney et al. | 260/465.3 |
| 4,010,188 | 3/1977 | Grasselli et al. | 260/465 C |
| 4,767,739 | 8/1988 | Glaeser et al. | 502/209 |
| 4,784,979 | 11/1988 | Toft et al. | 502/8 |
| 4,837,233 | 6/1989 | Glaeser et al. | 502/204 |
| 4,877,764 | 10/1989 | Glaeser et al. | 502/209 |
| 4,879,264 | 11/1989 | Toft et al. | 502/8 |
| 5,094,989 | 3/1992 | Lynch et al. | 502/202 |

OTHER PUBLICATIONS

CA115:70944c Method ... of paraffins. Honda et al., p. 730, 1991.

Primary Examiner—Joseph McKane
Attorney, Agent, or Firm—Michael F. Esposito; David J. Untener

[57] ABSTRACT

The process for the ammoxidation of a $C_3$ to $C_5$ paraffinic hydrocarbon to its corresponding $\alpha,\beta$-unsaturated hydrocarbon comprising reacting the $C_3$ to $C_5$ paraffinic hydrocarbon with ammonia and oxygen in a fluid bed reactor at a temperature of between 250° C. to 600° C. in the presence of a catalyst having the empirical formula as follows:

$$V_v Sb_m A_a D_d O_x$$

wherein A when present is Sn and/or Ti;

D when present is one or more of Li, Mg, Na, Ca, Sr, Ba, Co, Fe, Cr, Ga, Ni, Zn, Ge, Nb, Zr, Mo, W, Cu, Te, Ta, Se, Bi, Ce, In, As, B, Al, P and Mn; and wherein v is 1, m is 0.5–75, a is 0 to 25, d is 0 to 25, and x is determined by the oxidation state of the cations present, and a minor quantity of an halogen-containing component, preferably characterized by the following formula:

$$R\text{—}X \text{ or } X_2$$

where R=Hydrogen, $C_1$–$C_{20}$ alkyl and X=F, Cl, Br, I or mixtures thereof.

12 Claims, No Drawings

PARAFFIN AMMOXIDATION USING VANADIUM ANTIMONY OXIDE BASED CATALYSTS WITH HALIDE PROMOTERS

BACKGROUND OF THE INVENTION

1. Field of the Invention

The invention relates to an improved process for the catalytic ammoxidation of paraffins containing from 3 to 5 carbon atoms to α,β-unsaturated mono-nitriles, especially paraffins containing 3 to 4 carbon atoms. In particular, the present invention is directed to the ammoxidation of isobutane to methacrylonitrile and especially of propane to acrylonitrile.

Because of the price differential between propylene and propane, an economic incentive exists for the development of a viable catalytic process for conversion of propane to acrylonitrile.

Previous attempts to develop an efficient process for the ammoxidation of propane to acrylonitrile produced either insufficient yields of acrylonitrile or processes wherein the catalyst used for the reaction did not have sufficient lifetime characteristics to make the process economical. For example, U.S. Pat. Nos. 4,000,178, 3,833,638, 4,010,188 and 3,746,737 are related to the ammoxidation of propane to acrylonitrile using various types of catalyst systems wherein an halogen promoter is used during the reaction. In addition, Great Britain Patent 1,333,639 relates to ammoxidation of propane using a bismuthmolybdenum catalyst system and a halogen promoter. In each of these cases, either the catalyst utilized does not have a sufficient lifetime characteristic to make the process economically viable or the yields of acrylonitrile obtained during the process are unattractive from a commercial standpoint.

More recently, U.S. Pat. Nos. 4,767,739; 4,784,979; 4,879,264; 5,094,989; 4,837,233; and 4,877,764 are directed to propane ammoxidation to acrylonitrile utilizing mixed metal oxide catalyst and novel procedures for processes for preparing these catalyst which produce improved yield. However, these systems can be improved and the present invention is directed to such an improvement.

SUMMARY OF THE INVENTION

It is an object of the present invention to provide an improved process for the ammoxidation of paraffins to unsaturated nitriles.

It is a further object of the present invention to provide a fluid bed catalytic process for the conversion of propane to acrylonitrile.

Other objects, as well as aspects, features and advantages of the present invention will become apparent from the studying of the accompanying disclosure and the claims.

The foregoing and other objects of the present invention are achieved by the process of the present invention, which comprises the process for the ammoxidation of a $C_3$ to $C_5$ paraffinic hydrocarbon to the corresponding unsaturated nitrile. The process comprises reacting a $C_3$ to $C_5$ paraffinic hydrocarbon with ammonia and oxygen at a temperature of between 250° C. to 600° C. in the presence of a catalyst having the empirical formula as follows:

$$V_vSb_mA_aD_dO_x$$

wherein A when present is Sn and/or Ti
D when present is one or more of Li, Mg, Na, Ca, Sr, Ba, Co, Fe, Cr, Ga, Ni, Zn, Ge, Nb, Zr, Mo, W, Cu, Te, Ta, Se, Bi, Ce, In, As, B, Al, P and Mn
and wherein v is 1, m is 0.5–75, a is 0 to 25, d is 0 to 25, and x is determined by the oxidation state of the cations present, and a minor quantity of an halogen-containing component. Preferably, the halogen containing component is characterized by the following formula:

$$R\text{—}X \text{ or } X_2,$$

where R=Hydrogen, $C_1$-$C_{20}$ alkyl,
and X=F, Cl, Br, I or mixtures thereof.

In a preferred embodiment of the present invention the paraffinic hydrocarbon is selected from the group consisting of isobutane, propane, most preferably propane. In another aspect of the present invention the feed may comprise a mixture of propane and propylene.

In a still further preferred embodiment of the present invention the halide component is present in the feed mixture in an amount of between 10 to 10,000 ppm. Preferably, the halide component is present in an amount of between 15 to 5,000 ppm, most preferably between 20 to 1,000 ppm.

In another preferred embodiment of the process of the present invention, the ratio of the oxygen-containing gas to paraffin is between about 0.1:1 and 5:1. The ratio of ammonia to paraffin is between 0.1:1 and 5:1. Optionally, a diluent gas such as nitrogen may be added to the reactor. The typical ratio of diluent to paraffin in the reactor can range between 0 to 30:1. The process can be operated at an elevated temperature of between 250° C. to 800° C., preferably between 400° C. to 650° C. and, most preferably, between about 460° C. to 520° C.

DETAILED DESCRIPTION OF THE INVENTION

The process of the present invention is directed to the method of preparing acrylonitrile from propane or propane/propylene mixtures and methacrylonitrile from isobutane or isobutane/isobutylene mixtures. The process comprises reacting the paraffinic hydrocarbon with ammonia in an oxygen-containing-gas (preferably air) over a vanadium antimony oxide based catalyst in the presence of one or more halide compounds.

The catalysts useful in the process of the present invention are described by the following empirical formula:

$$V_vSb_mA_aD_dO_x$$

wherein A when present is Sn and/or Ti
D when present is one or more of Li, Mg, Na, Ca, Sr, Ba, Co, Fe, Cr, Ga, Ni, Zn, Ge, Nb, Zr, Mo, W, Cu, Te, Ta, Se, Bi, Ce, In, As, B, Al, P and Mn
and wherein v is 1, m is 0.5–75, a is 0 to 25, d is 0 to 25, and x is determined by the oxidation state of the cations present, preferably m is 0.5 to 50, a is greater than 0 to 20 and d is greater than 0 to 20, especially preferred being m equal to 0.5 to 40, a equal to 0.01 to 15 and d equal to 0.01 to 15, and a minor quantity of an halogen-containing component, preferably characterized by the following formula:

$$R\text{—}X \text{ or } X_2$$

where R=Hydrogen, $C_1$-$C_{20}$ alkyl and X=F, Cl, Br, I or mixtures thereof.

These above-mentioned vanadium antimony oxide based catalysts may be prepared by methods known in the art. In particular, an effective method of preparation is the peroxide method disclosed in U.S. Pat. Nos. 4,784,979 and 4,879,264, herein incorporated by reference. In general, the method disclosed in these patents comprises making a catalyst precursor by reacting the $VO(O_2)+$ with an antimony compound containing antimony in the valence state of 3+. Typically the vanadium ion is made by reacting hydrogen peroxide with a vanadium compound. This precursor is then dried and calcined typically by spray drying to form microspheroidal catalyst particles. In addition, the catalyst may optionally be washed at any one of the points in the procedure of making it as disclosed in U.S. Pat. Nos. 3,860,534 and 5,094,989 herein incorporated by reference. Moreover, the catalyst may be treated by the methods disclosed in U.S. Ser. No. 112,027 and 213,325, and U.S. Ser. No. 304,029, assigned to the assignee of the present invention, herein incorporated by reference. The catalyst may be unsupported or supported on a suitable carrier. Preferably the catalyst is supported on a carrier such as silica, alumina, zirconia and/or mixtures thereof.

The halide compounds as described in the formula below:

$$R-X \text{ or } X_2$$

where R=Hydrogen, $C_1$–$C_{20}$ alkyl
and X=F, Cl, Br, I
are present in the reactor in the amount of between 10 to about 10,000 ppm. Typically, the halide compound is fed to the reactor along with the paraffin, ammonia and oxygen-containing gas. Suitable halide-containing compounds useful in the practice of the present invention are hydrogen bromide, hydrogen chloride, hydrogen iodide and hydrogen fluoride along with halide-alkanes such as methylbromide, methylchloride, methyliodide, methylfluoride, ethylbromide, ethylfluoride, ethyliodide, and the like. The preferred halide component is typically hydrogen bromide.

The contact time for the reaction would depend upon various factors, among them being the catalyst used in the surface area and the physical and chemical characteristics of the product desired. However, in general the contact times are short ranging from 0.1 to 20 seconds, preferably between 0.1 to 5 seconds, most preferably being 0.1 to 3 seconds. The following examples of the process of the present invention are set forth below for illustration purposes only. The examples in Table 1 set forth the unexpectedly high yields of selectivities of the process of the present invention combined with the unexpectedly stable performance during operation.

TABLE 1

| | Catalyst Composition | Halide Promoter (ppm) | Reaction Temperature (°C.) | Contact Time (sec.) | % Propane Conversion | % Acrylonitrile Selectivity |
|---|---|---|---|---|---|---|
| Comparative 1 | EMPTY REACTOR | None 0 | 480 | 3.36 | 0.9 | 4.3 |
| Comparative 2 | EMPTY REACTOR | HBr 378 | 480 | 3.36 | 2.2 | 1.1 |
| Comparative 3 | Quartz Chips | HBr 378 | 480 | 3.17 | 1.7 | 0.0 |
| Comparative 4 | $VSb_{1.4}Sn_{0.2}Ti_{0.1}O_x$ | None 0 | 480 | 3.02 | 41.7 | 42.7 |
| Example 1 | $VSb_{1.4}Sn_{0.2}Ti_{0.1}O_x$ | $C_2H_5Br$ 1363 | 470 | 2.06 | 90.7 | 46.8 |
| Example 2 | $VSb_{1.4}Sn_{0.2}Ti_{0.1}O_x$ | HBr 1363 | 470 | 2.10 | 87.3 | 50.8 |
| Example 3 | $VSb_{1.4}Sn_{0.2}Ti_{0.1}O_x$ | HBr 351 | 470 | 4.28 | 89.0 | 48.1 |
| Example 4 | $VSb_{1.4}Sn_{0.2}Ti_{0.1}O_x$ | HBr 1359 | 470 | 2.95 | 94.2 | 45.9 |
| Example 5 | $VSb_{1.4}Sn_{0.2}Ti_{0.1}O_x$ | HBr 1847 | 450 | 2.94 | 90.4 | 50.1 |
| Example 6 | $VSb_{1.4}Sn_{0.2}Ti_{0.1}O_x$ | HBr 2607 | 460 | 1.76 | 87.5 | 48.1 |
| Comparative 5 | $VSb_{1.4}Sn_{0.2}Ti_{0.1}O_x$ | None 0 | 480 | 3.59 | 29.9 | 55.7 |
| Example 7 | $VSb_{1.4}Sn_{0.2}Ti_{0.1}O_x$ | HBr 78 | 480 | 2.10 | 31.8 | 59.6 |
| Example 8 | $VSb_{1.4}Sn_{0.2}Ti_{0.1}O_x$ | HBr 138 | 460 | 3.39 | 30.1 | 61.6 |
| Comparative 6 | $VSb_{1.4}Sn_{0.2}Ti_{0.1}O_x$ | None 0 | 460 | 4.06 | 24.4 | 56.8 |
| Example 9 | $VSb_{1.4}Sn_{0.2}Ti_{0.1}O_x$ | HBr 173 | 460 | 4.13 | 31.3 | 60.0 |
| Example 10 | $VSb_{1.2}Sn_{0.5}Ti_{1.0}Fe_{0.12}O_x + 40\%\ SiO_2$ | $C_2H_5Br$ 1982 | 460 | 1.36 | 89.8 | 43.3 |
| Example 11 | $VSb_{1.2}Sn_{0.5}Ti_{1.0}Fe_{0.12}O_x + 40\%\ SiO_2$ | HBr 951 | 480 | 1.87 | 87.9 | 37.3 |
| Example 12 | $VSb_{1.2}Sn_{0.5}Ti_{1.0}Fe_{0.12}O_x + 40\%\ SiO_2$ | HBr 534 | 480 | 1.25 | 85.2 | 55.1 |
| Example 13 | $VSb_{1.2}Sn_{0.5}Ti_{1.0}Fe_{0.12}O_x + 40\%\ SiO_2$ | HBr 511 | 480 | 1.60 | 87.2 | 52.2 |
| Example 14 | $[VSb_{1.4}Sn_{0.2}Ti_{0.1}O_x + Sb_{0.2}]Co_{0.001}$ | HBr 1343 | 470 | 2.56 | 92.5 | 48.2 |
| Example 15 | $[VSb_{1.4}Sn_{0.2}Ti_{0.1}O_x + Sb_{0.2}]Co_{0.005}$ | HBr 38 | 480 | 2.06 | 29.2 | 63.6 |
| Example 16 | $[VSb_{1.4}Sn_{0.2}Ti_{0.1}O_x + Sb_{0.2}]Co_{0.005}$ | HBr | 480 | 2.14 | 30.0 | 63.0 |

TABLE 1-continued

| | | | | | | |
|---|---|---|---|---|---|---|
| Example 17 | $VSb_{1.6}Sn_{0.2}Ti_{0.01}O_x$ | 73 HBr 1037 | 480 | 2.15 | 92.1 | 43.8 |
| Example 18 | $VSb_{2.0}Sn_{0.25}O_x$ | HBr 1903 | 470 | 1.76 | 91.5 | 42.7 |
| Example 19 | $VSb_{36}Sn_{12}Cu_{3.8}Te_{1.7}W_{0.7}O_x$ | HBr 1902 | 460 | 3.78 | 95.0 | 46.0 |
| Comparative 7 | $VSb_{1.4}Sn_{0.2}Ti_{0.1}O_x$ | None 0 | 480 | 3.59 | 40.3 | 47.5 |
| Example 20 | $VSb_{1.4}Sn_{0.2}Ti_{0.1}O_x$ | $CCl_4$ 474 | 480 | 3.52 | 54.0 | 47.4 |
| Example 21 | $VSb_{1.4}Sn_{0.2}Ti_{0.1}O_x$ | $CCl_4$ 946 | 480 | 3.57 | 60.9 | 46.8 |
| Example 22 | $VSb_{1.4}Sn_{0.2}Ti_{0.1}O_x$ | $CHCl_3$ 1314 | 480 | 3.51 | 57.8 | 45.3 |

| | Catalyst Composition | % Acrylontrile Yield | Feed Composition |
|---|---|---|---|
| Comparative 1 | EMPTY REACTOR | 0.04 | $1C_3H_8/1.16NH_3/2.87O_2/10.22N_2/2.97H_2O$ |
| Comparative 2 | EMPTY REACTOR | 0.02 | $1C_3H_8/1.16NH_3/2.87O_2/10.22N_2/2.97H_2O$ |
| Comparative 3 | Quartz Chips | 0.00 | $1C_3H_8/1.16NH_3/2.87O_2/10.22N_2/2.97H_2O$ |
| Comparative 4 | $VSb_{1.4}Sn_{0.2}Ti_{0.1}O_x$ | 17.78 | $1C_3H_8/1.16NH_3/2.87O_2/10.22N_2/2.97H_2O$ |
| Example 1 | $VSb_{1.4}Sn_{0.2}Ti_{0.1}O_x$ | 42.48 | $1C_3H_8/1.25NH_3/2.98O_2/10.68N_2/2.91H_2O$ |
| Example 2 | $VSb_{1.4}Sn_{0.2}Ti_{0.1}O_x$ | 44.30 | $1C_3H_8/1.25NH_3/2.98O_2/10.68N_2/2.91H_2O$ |
| Example 3 | $VSb_{1.4}Sn_{0.2}Ti_{0.1}O_x$ | 42.81 | $1C_3H_8/1.16NH_3/2.99O_2/10.75N_2/2.88H_2O$ |
| Example 4 | $VSb_{1.4}Sn_{0.2}Ti_{0.1}O_x$ | 43.21 | $1C_3H_8/1.25NH_3/2.99O_2/10.69N_2/2.91H_2O$ |
| Example 5 | $VSb_{1.4}Sn_{0.2}Ti_{0.1}O_x$ | 45.29 | $1C_3H_8/1.24NH_3/2.97O_2/10.65N_2/3.05H_2O$ |
| Example 6 | $VSb_{1.4}Sn_{0.2}Ti_{0.1}O_x$ | 42.12 | $1C_3H_8/1.34NH_3/2.97O_2/10.65N_2/2.93H_2O$ |
| Comparative 5 | $VSb_{1.4}Sn_{0.2}Ti_{0.1}O_x$ | 16.68 | $3C_3H_8/1.20NH_3/2.88O_2/10.04N_2/1.86H_2O$ |
| Example 7 | $VSb_{1.4}Sn_{0.2}Ti_{0.1}O_x$ | 18.92 | $3C_3H_8/1.41NH_3/2.82O_2/9.70N_2/1.91H_2O$ |
| Example 8 | $VSb_{1.4}Sn_{0.2}Ti_{0.1}O_x$ | 18.54 | $3C_3H_8/1.22NH_3/3.03O_2/10.82N_2/3.69H_2O$ |
| Comparative 6 | $VSb_{1.4}Sn_{0.2}Ti_{0.1}O_x$ | 13.85 | $3C_3H_8/1.21NH_3/3.03O_2/2.91N_2/1.37H_2O$ |
| Example 9 | $VSb_{1.4}Sn_{0.2}Ti_{0.1}O_x$ | 18.80 | $3C_3H_8/1.24NH_3/3.03O_2/2.91N_2/1.40H_2O$ |
| Example 10 | $VSb_{1.2}Sn_{0.5}Ti_{1.0}Fe_{0.12}O_x$ + 40% $SiO_2$ | 38.86 | $1C_3H_8/1.23NH_3/3.20O_2/11.41N_2/3.30H_2O$ |
| Example 11 | $VSb_{1.2}Sn_{0.5}Ti_{1.0}Fe_{0.12}O_x$ + 40% $SiO_2$ | 32.78 | $1C_3H_8/1.30NH_3/3.00O_2/10.65N_2/5.05H_2O$ |
| Example 12 | $VSb_{1.2}Sn_{0.5}Ti_{1.0}Fe_{0.12}O_x$ + 40% $SiO_2$ | 46.88 | $0.419C_3H_8/0.581C_3H_6/1.3NH_3/2.94O_2/10.45N_2/3.02H_2O$ |
| Example 13 | $VSb_{1.2}Sn_{0.5}Ti_{1.0}Fe_{0.12}O_x$ + 40% $SiO_2$ | 45.50 | $0.417C_3H_8/0.583C_3H_6/1.3NH_3/2.90O_2/10.31N_2/4.04H_2O$ |
| Example 14 | $[VSb_{1.4}Sn_{0.2}Ti_{0.1}O_x + Sb_{0.2}]Co_{0.001}$ | 44.60 | $1C_3H_8/1.28NH_3/2.92O_2/10.44N_2/2.80H_2O$ |
| Example 15 | $[VSb_{1.4}Sn_{0.2}Ti_{0.1}O_x + Sb_{0.2}]Co_{0.005}$ | 18.59 | $3C_3H_8/1.66NH_3/2.83O_2/9.97N_2/1.90H_2O$ |
| Example 16 | $[VSb_{1.4}Sn_{0.2}Ti_{0.1}O_x + Sb_{0.2}]Co_{0.005}$ | 18.91 | $3C_3H_8/1.66NH_3/2.83O_2/9.97N_2/1.89H_2O$ |
| Example 17 | $VSb_{1.6}Sn_{0.2}Ti_{0.01}O_x$ | 40.37 | $1C_3H_8/1.28NH_3/2.92O_2/10.44N_2/3.48H_2O$ |
| Example 18 | $VSb_{2.0}Sn_{0.25}O_x$ | 39.04 | $1C_3H_8/1.28NH_3/3.00O_2/10.67N_2/3.13H_2O$ |
| Example 19 | $VSb_{36}Sn_{12}Cu_{3.8}Te_{1.7}W_{0.7}O_x$ | 43.67 | $1C_3H_8/1.15NH_3/3.33O_2/10.70N_2/3.22H_2O$ |
| Comparative 7 | $VSb_{1.4}Sn_{0.2}Ti_{0.1}O_x$ | 19.12 | $1C_3H_8/1.18NH_3/2.92O_2/10.46N_2/0.00H_2O$ |
| Example 20 | $VSb_{1.4}Sn_{0.2}Ti_{0.1}O_x$ | 25.60 | $1C_3H_8/1.18NH_3/2.92O_2/10.46N_2/0.00H_2O$ |
| Example 21 | $VSb_{1.4}Sn_{0.2}Ti_{0.1}O_x$ | 28.48 | $1C_3H_8/1.18NH_3/2.92O_2/10.46N_2/0.00H_2O$ |
| Example 22 | $VSb_{1.4}Sn_{0.2}Ti_{0.1}O_x$ | 26.15 | $1C_3H_8/1.16NH_3/2.89O_2/10.32N_2/0.00H_2O$ |

What we claim as our invention is:

1. The process for the ammoxidation of a $C_3$ to $C_5$ paraffinic hydrocarbon to its corresponding α,β-unsaturated hydrocarbon comprising reacting the $C_3$ to $C_5$ paraffinic hydrocarbon with ammonia and oxygen in a fluid bed reactor at a temperature of between 250° C. to 600° C. in the presence of a catalyst having the empirical formula as follows:

$$V_vSb_mA_aD_dO_x$$

wherein A when present is Sn and/or Ti;
D when present is one or more of Li, Mg, Na, Ca, Sr, Ba, Co, Fe, Cr, Ga, Ni, Zn, Ge, Nb, Zr, Mo, W, Cu, Te, Ta, Se, Bi, Ce, In, As, B, Al, P and Mn; and
wherein v is 1, m is 0.5–75, a is 0 to 25, d is 0 to 25, and x is determined by the oxidation state of the cations present, and a minor quantity of an halogen-containing component.

2. The process of claim 1 wherein the halogen-containing component is the following formula:

R—X where R=Hydrogen, $C_1$-$C_{20}$ alkyl
and X=F, Cl, Br, I or mixtures thereof.

3. The process of claim 1 wherein the halogen containing component is the following formula:

$$X_2$$

where X=F, Cl, Br, I or mixtures thereof.

4. The process of claim 1 wherein the paraffinic hydrocarbon is selected from the group consisting of isobutane and propane.

5. The process of claim 4 wherein the paraffinic hydrocarbon is propane.

6. The process of claim 1 wherein the halogen containing compound is present in the feed mixture in an amount of between 10 to 10,000 ppm.

7. The process of claim 6 wherein the halogen containing compound is present in an amount of between 15 to 5,000 ppm.

8. The process of claim 7 wherein the halogen containing compound is present in an amount between 20 to 1,000 ppm.

9. The process of claim 2 wherein the halogen containing compound is selected from the group consisting of hydrogen bromide, hydrogen chloride, methyl bromine, methyl chloride, hydrogen iodide, hydrogen fluorine, methyl iodide and methyl fluorine.

10. The process of claim 9 wherein the halogen containing compound is selected to be hydrogen bromide.

11. The process of claim 1 wherein the halogen containing compound is added to the reactor along with the paraffinic hydrocarbon, ammonia and oxygen.

12. The process of claim 1 wherein the halogen containing compound is added to the catalyst.

* * * * *